United States Patent
Supper et al.

(10) Patent No.: US 9,480,587 B2
(45) Date of Patent: Nov. 1, 2016

(54) IMPLANT WITH ATTACHED ELEMENT AND METHOD OF MAKING SUCH AN IMPLANT

(71) Applicant: Angiomed GmbH & Co. Medizintechnik KG, Karlsruhe (DE)

(72) Inventors: Wolfgang Supper, Karlsruhe (DE); Walter Gamer, Bruchsal (DE)

(73) Assignee: ANGIOMED GMBH & CO. MEDIZINTECHNIK KG, Karlsruhe (DE)

( * ) Notice: Subject to any disclaimer, the term of this patent is extended or adjusted under 35 U.S.C. 154(b) by 0 days.

(21) Appl. No.: 14/495,820

(22) Filed: Sep. 24, 2014

(65) Prior Publication Data

US 2015/0073532 A1 Mar. 12, 2015

Related U.S. Application Data

(63) Continuation of application No. 13/279,189, filed on Oct. 21, 2011, now Pat. No. 8,900,290, which is a continuation of application No. 10/362,040, filed as application No. PCT/EP01/09467 on Aug. 16, 2001, now Pat. No. 8,043,364.

(30) Foreign Application Priority Data

Aug. 17, 2000 (GB) .................... 0020491.7

(51) Int. Cl.
*A61F 2/82* (2013.01)
*A61F 2/89* (2013.01)
(Continued)

(52) U.S. Cl.
CPC . *A61F 2/89* (2013.01); *A61F 2/91* (2013.01); *A61F 2/915* (2013.01); *A61L 31/18* (2013.01);
(Continued)

(58) Field of Classification Search
CPC ...... A61F 2/82; A61F 2/90; A61F 2002/826; A61F 2002/828; A61F 2/852; A61F 2/89; A61F 13/44; A61F 2250/0032; A61F 2250/0096–2250/0098; A61F 2002/30056; A61F 2002/3008; A61F 2/91; A61F 2/95
See application file for complete search history.

(56) References Cited

U.S. PATENT DOCUMENTS 5,091,205 A 2/1992 Fan
5,312,456 A * 5/1994 Reed .................... A61F 2/82
24/442
(Continued)

FOREIGN PATENT DOCUMENTS

DE 04130431 A1 3/1993
DE 29621207 U1 1/1997
(Continued)

OTHER PUBLICATIONS

U.S. Appl. No. 12/594,531, filed Oct. 2, 2009 Non-Final Office Action dated Oct. 2, 2012.
(Continued)

*Primary Examiner* — Christopher D Prone
(74) *Attorney, Agent, or Firm* — C.R. Bard Intellectual Property; Buchalter Nemer

(57) ABSTRACT

A stent having an axial end to which is attached a ring of spoons of a material different from that of the stent. In one aspect, the ring of spoons is connected to the axial end through a plurality of complementary male-female form-fitting portions. In one aspect, the ring of spoons include parallel straight side edges. In one aspect, each of the side edges lies within a first distance from a facing side edge of an adjacent spoon in a stent delivery configuration, and each of the side edges lies within a second distance, greater than the first distance, from the facing side edge of an adjacent spoon in a stent deployed configuration.

12 Claims, 3 Drawing Sheets

(51) Int. Cl.
*A61F 2/91* (2013.01)
*A61F 2/915* (2013.01)
*A61L 31/18* (2006.01)
*A61F 2/966* (2013.01)

(52) U.S. Cl.
CPC ............... *A61F 2002/91508* (2013.01); *A61F 2002/91525* (2013.01); *A61F 2002/91541* (2013.01); *A61F 2002/91558* (2013.01); *A61F 2002/9665* (2013.01); *A61F 2220/005* (2013.01); *A61F 2220/0058* (2013.01); *A61F 2230/0054* (2013.01); *A61F 2230/0067* (2013.01); *A61F 2250/0039* (2013.01); *A61F 2250/0098* (2013.01)

(56) References Cited

U.S. PATENT DOCUMENTS

| | | | |
|---|---|---|---|
| 5,464,419 A | 11/1995 | Glastra | |
| 5,527,353 A | 6/1996 | Schmitt | |
| 5,591,223 A | 1/1997 | Lock et al. | |
| 5,645,532 A | 7/1997 | Horgan | |
| 5,725,572 A | 3/1998 | Lam et al. | |
| 5,741,327 A | 4/1998 | Frantzen | |
| 5,759,192 A | 6/1998 | Saunders | |
| 5,800,511 A | 9/1998 | Mayer | |
| 5,824,042 A | 10/1998 | Lombardi et al. | |
| 5,824,059 A | 10/1998 | Wijay | |
| 5,824,077 A | 10/1998 | Mayer | |
| 5,843,118 A | 12/1998 | Sepetka et al. | |
| 5,858,556 A | 1/1999 | Eckert et al. | |
| 5,861,027 A * | 1/1999 | Trapp | A61F 2/91 606/191 |
| 5,868,783 A | 2/1999 | Tower | |
| 5,922,020 A | 7/1999 | Klein et al. | |
| 6,022,374 A * | 2/2000 | Imran | A61F 2/91 623/1.34 |
| 6,053,940 A | 4/2000 | Wijay | |
| 6,056,187 A | 5/2000 | Acciai et al. | |
| 6,086,611 A | 7/2000 | Duffy et al. | |
| 6,099,561 A | 8/2000 | Alt | |
| 6,174,329 B1 | 1/2001 | Callol et al. | |
| 6,241,762 B1 | 6/2001 | Shanley | |
| 6,270,524 B1 | 8/2001 | Kim | |
| 6,293,966 B1 | 9/2001 | Frantzen | |
| 6,312,456 B1 * | 11/2001 | Kranz | A61F 2/91 623/1.13 |
| 6,334,871 B1 | 1/2002 | Dor et al. | |
| 6,355,057 B1 | 3/2002 | DeMarais et al. | |
| 6,379,381 B1 | 4/2002 | Hossainy et al. | |
| 6,387,123 B1 | 5/2002 | Jacobs et al. | |
| 6,409,752 B1 | 6/2002 | Boatman et al. | |
| 6,451,047 B2 | 9/2002 | McCrea et al. | |
| 6,471,721 B1 | 10/2002 | Dang | |
| 6,475,233 B2 | 11/2002 | Trozera | |
| 6,478,816 B1 | 11/2002 | Kveen et al. | |
| 6,540,777 B2 | 4/2003 | Stenzel et al. | |
| 6,547,818 B1 | 4/2003 | Rourke et al. | |
| 6,562,065 B1 | 5/2003 | Shanley | |
| 6,585,757 B1 | 7/2003 | Callol | |
| 6,605,110 B2 | 8/2003 | Harrison | |
| 6,629,994 B2 | 10/2003 | Gomez et al. | |
| 6,676,700 B1 | 1/2004 | Jacobs et al. | |
| 6,770,089 B1 | 8/2004 | Hong et al. | |
| 6,797,217 B2 | 9/2004 | McCrea et al. | |
| 6,827,734 B2 | 12/2004 | Fariabi | |
| 6,878,162 B2 | 4/2005 | Bales et al. | |
| 6,979,346 B1 | 12/2005 | Hossainy et al. | |
| 7,060,093 B2 | 6/2006 | Dang et al. | |
| 7,135,038 B1 | 11/2006 | Limon | |
| 7,175,654 B2 | 2/2007 | Bonsignore et al. | |
| 7,381,217 B2 | 6/2008 | Tischler | |
| 7,462,190 B2 | 12/2008 | Lombardi | |
| 7,468,071 B2 | 12/2008 | Edwin et al. | |
| 7,479,157 B2 | 1/2009 | Weber et al. | |
| 7,691,461 B1 | 4/2010 | Prabhu | |
| 7,771,463 B2 | 8/2010 | Ton et al. | |
| 7,772,659 B2 | 8/2010 | Rodmacq et al. | |
| 8,043,364 B2 | 10/2011 | Lombardi et al. | |
| 8,152,842 B2 | 4/2012 | Schlun | |
| 8,292,950 B2 | 10/2012 | Dorn et al. | |
| 8,322,593 B2 | 12/2012 | Wack | |
| 8,403,978 B2 | 3/2013 | Schlun et al. | |
| 8,475,520 B2 | 7/2013 | Wack et al. | |
| 8,500,793 B2 | 8/2013 | Zipse et al. | |
| 8,518,101 B2 | 8/2013 | Dreher | |
| 8,551,156 B2 | 10/2013 | Wack et al. | |
| 8,574,286 B2 | 11/2013 | Wack | |
| 8,721,709 B2 | 5/2014 | Schlun et al. | |
| 2002/0007212 A1 | 1/2002 | Brown et al. | |
| 2002/0116044 A1 | 8/2002 | Cottone et al. | |
| 2002/0116051 A1 | 8/2002 | Cragg | |
| 2002/0138136 A1 | 9/2002 | Chandresekaran et al. | |
| 2002/0193867 A1 | 12/2002 | Gladdish et al. | |
| 2002/0193869 A1 | 12/2002 | Dang | |
| 2002/0198589 A1 | 12/2002 | Leong | |
| 2003/0055485 A1 | 3/2003 | Lee et al. | |
| 2003/0135254 A1 | 7/2003 | Curcio et al. | |
| 2003/0144725 A1 | 7/2003 | Lombardi | |
| 2003/0216807 A1 | 11/2003 | Jones et al. | |
| 2003/0225448 A1 | 12/2003 | Gerberding | |
| 2004/0015228 A1 | 1/2004 | Lombardi et al. | |
| 2004/0015229 A1 | 1/2004 | Fulkerson et al. | |
| 2004/0034402 A1 | 2/2004 | Bales et al. | |
| 2004/0044401 A1 | 3/2004 | Bales et al. | |
| 2004/0073290 A1 | 4/2004 | Chouinard | |
| 2004/0073291 A1 | 4/2004 | Brown et al. | |
| 2004/0117002 A1 | 6/2004 | Girton et al. | |
| 2004/0230293 A1 | 11/2004 | Yip et al. | |
| 2004/0236400 A1 | 11/2004 | Edwin et al. | |
| 2004/0236409 A1 | 11/2004 | Pelton et al. | |
| 2004/0254637 A1 | 12/2004 | Yang et al. | |
| 2005/0049682 A1 | 3/2005 | Leanna et al. | |
| 2005/0060025 A1 | 3/2005 | Mackiewicz et al. | |
| 2005/0149168 A1 | 7/2005 | Gregorich | |
| 2005/0172471 A1 | 8/2005 | Vietmeier | |
| 2005/0182477 A1 | 8/2005 | White | |
| 2005/0222667 A1 | 10/2005 | Hunt | |
| 2005/0278019 A1 | 12/2005 | Gregorich | |
| 2006/0030934 A1 | 2/2006 | Hogendijk et al. | |
| 2006/0064153 A1 | 3/2006 | Langhans et al. | |
| 2006/0216431 A1 | 9/2006 | Kerrigan | |
| 2006/0241741 A1 | 10/2006 | Lootz | |
| 2006/0265049 A1 | 11/2006 | Gray et al. | |
| 2007/0112421 A1 | 5/2007 | O'Brien | |
| 2007/0219624 A1 | 9/2007 | Brown et al. | |
| 2008/0051885 A1 | 2/2008 | Llanos et al. | |
| 2008/0188924 A1 | 8/2008 | Prabhu | |
| 2009/0125092 A1 | 5/2009 | McCrea et al. | |
| 2009/0125099 A1 | 5/2009 | Weber et al. | |
| 2009/0200360 A1 | 8/2009 | Wack | |
| 2009/0204203 A1 | 8/2009 | Allen et al. | |
| 2009/0264982 A1 | 10/2009 | Krause et al. | |
| 2010/0016949 A1 | 1/2010 | Wack | |
| 2010/0070021 A1 | 3/2010 | Wack et al. | |
| 2010/0114298 A1 | 5/2010 | Dorn et al. | |
| 2010/0191321 A1 | 7/2010 | Schlun et al. | |
| 2010/0204784 A1 | 8/2010 | Molaei et al. | |
| 2010/0211161 A1 | 8/2010 | Dreher | |
| 2010/0234936 A1 | 9/2010 | Schlun | |
| 2010/0249903 A1 | 9/2010 | Wack et al. | |
| 2010/0298921 A1 | 11/2010 | Schlun et al. | |
| 2011/0196473 A1 | 8/2011 | McCrea et al. | |
| 2011/0198327 A1 | 8/2011 | Prabhu | |
| 2011/0245905 A1 | 10/2011 | Weber et al. | |
| 2011/0319977 A1 | 12/2011 | Pandelidis et al. | |
| 2012/0041542 A1 | 2/2012 | Lombardi et al. | |
| 2014/0033790 A1 | 2/2014 | Wack et al. | |

(56) References Cited

U.S. PATENT DOCUMENTS

| | | | |
|---|---|---|---|
| 2014/0067045 A1 | 3/2014 | Wack | |
| 2014/0239050 A1 | 8/2014 | Schlun et al. | |

FOREIGN PATENT DOCUMENTS

| | | | |
|---|---|---|---|
| DE | 19728337 A1 | 1/1999 | |
| DE | 29904817 U1 | 5/1999 | |
| DE | 10201151 A1 | 7/2003 | |
| DE | 202004014789 U1 | 1/2005 | |
| DE | 102004045994 A1 | 3/2006 | |
| EP | 0481365 A1 | 4/1992 | |
| EP | 0709068 A2 | 5/1996 | |
| EP | 0800800 A1 | 10/1997 | |
| EP | 0847733 A1 | 6/1998 | |
| EP | 0870483 A2 | 10/1998 | |
| EP | 1029517 A2 | 8/2000 | |
| EP | 1034751 A2 | 9/2000 | |
| EP | 1157673 A2 | 11/2001 | |
| EP | 1190685 A2 | 3/2002 | |
| EP | 1212991 A2 | 6/2002 | |
| EP | 1245203 A2 | 10/2002 | |
| EP | 1255507 A1 | 11/2002 | |
| EP | 1356789 A1 | 10/2003 | |
| EP | 1433438 A2 | 6/2004 | |
| EP | 1488763 A2 | 12/2004 | |
| EP | 1767240 A1 | 3/2007 | |
| EP | 2134301 A2 | 12/2009 | |
| FR | 2626046 A1 | 7/1989 | |
| GB | 453944 A | 9/1936 | |
| JP | 07315147 A | 12/1995 | |
| JP | 2004-506477 A | 3/2004 | |
| JP | 2007-504891 A | 3/2007 | |
| JP | 4827965 B2 | 11/2011 | |
| JP | 4933018 B2 | 5/2012 | |
| WO | 9417754 A1 | 8/1994 | |
| WO | 9503010 A1 | 2/1995 | |
| WO | 9626689 A1 | 9/1996 | |
| WO | 9733534 A1 | 9/1997 | |
| WO | 9820810 A1 | 5/1998 | |
| WO | 9915108 A2 | 4/1999 | |
| WO | 9938457 A1 | 8/1999 | |
| WO | 9949928 A1 | 10/1999 | |
| WO | 9955253 A1 | 11/1999 | |
| WO | 0045742 A1 | 8/2000 | |
| WO | 0049971 A1 | 8/2000 | |
| WO | 0064375 A1 | 11/2000 | |
| WO | 0101889 A1 | 1/2001 | |
| WO | 0132102 A1 | 5/2001 | |
| WO | 0158384 A1 | 8/2001 | |
| WO | 0176508 A2 | 10/2001 | |
| WO | 0215820 A2 | 2/2002 | |
| WO | 0249544 A1 | 6/2002 | |
| WO | 03055414 A1 | 7/2003 | |
| WO | 03075797 | 9/2003 | |
| WO | 03101343 A1 | 12/2003 | |
| WO | 2004019820 A1 | 3/2004 | |
| WO | 2004028408 A1 | 4/2004 | |
| WO | 2004032802 A2 | 4/2004 | |
| WO | 2004058384 A1 | 7/2004 | |
| WO | 2005067816 A1 | 7/2005 | |
| WO | 2005072652 A1 | 8/2005 | |
| WO | 2005104991 A1 | 11/2005 | |
| WO | 2005032403 A3 | 12/2005 | |
| WO | 2006010636 A1 | 2/2006 | |
| WO | 2006010638 A1 | 2/2006 | |
| WO | 2006014768 A1 | 2/2006 | |
| WO | 2006025847 A2 | 3/2006 | |
| WO | 2006036912 A2 | 4/2006 | |
| WO | 2006047977 A1 | 5/2006 | |
| WO | 2006064153 A1 | 6/2006 | |
| WO | 2007073413 A1 | 6/2007 | |
| WO | 2006026778 A3 | 11/2007 | |
| WO | 2007131798 A1 | 11/2007 | |
| WO | 2007135090 A1 | 11/2007 | |
| WO | 2008006830 A1 | 1/2008 | |
| WO | 2008022949 A1 | 2/2008 | |
| WO | 2008022950 A1 | 2/2008 | |
| WO | 2008025762 A1 | 3/2008 | |
| WO | 2008028964 A2 | 3/2008 | |
| WO | 2008055980 A1 | 5/2008 | |
| WO | 2008068279 A1 | 6/2008 | |
| WO | 2008101987 A1 | 8/2008 | |
| WO | 2008119837 A2 | 10/2008 | |
| WO | 2009030748 A2 | 3/2009 | |

OTHER PUBLICATIONS

U.S. Appl. No. 12/676,584, filed Mar. 4, 2010 Non-Final Office Action dated May 24, 2013.
U.S. Appl. No. 12/676,584, filed Mar. 4, 2010 Notice of Allowance dated Dec. 27, 2013.
U.S. Appl. No. 13/279,189, filed Oct. 21, 2011 Examiner's Answer dated Feb. 14, 2014.
U.S. Appl. No. 13/279,189, filed Oct. 21, 2011 Final Office Action dated May 2, 2013.
U.S. Appl. No. 13/279,189, filed Oct. 21, 2011 Non-Final Office Action dated Oct. 17, 2012.
U.S. Appl. No. 13/975,147, filed Aug. 23, 2013 Non-Final Office Action dated May 15, 2014.
Database Wikipedia, Sep. 11, 2007, "Lumen (anatomy)" XP 002453737 abstract.
EP 07787316.4 filed Jul. 10, 2007 Examination Report dated Dec. 23, 2011.
EP 07802603.6 filed Aug. 14, 2007 Office Action dated Dec. 13, 2010.
EP 07820066.4 filed Mar. 31, 2009 Examination Report dated Dec. 27, 2011.
EP 09177588 filed Aug. 14, 2007 Search Report dated Aug. 12, 2011.
EP 12174308.2 filed Apr. 3, 2008 European Search Report dated Sep. 10, 2012.
JP 2010-523512 filed Sep. 5, 2008 Office Action dated Sep. 25, 2012.
PCT/EP2001/009467 International Preliminary Examination Report Sep. 17, 2002.
PCT/EP2001/009467 International Search Report dated Feb. 18, 2002.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.
PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/057041 filed Jul. 10, 2007 International Preliminary Report on Patentability dated Jan. 13, 2009.
PCT/EP2007/057041 filed Jul. 10, 2007 International Search Report dated Oct. 18, 2007.
PCT/EP2007/057041 filed Jul. 10, 2007 Written Opinion Jan. 10, 2009.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/058416 filed Aug. 14, 2007 International Preliminary Report on Patentability dated Feb. 24, 2009.
PCT/EP2007/058416 filed Aug. 14, 2007 International Search Report dated Nov. 22, 2007.
PCT/EP2007/058416 filed Aug. 14, 2007 Written Opinion dated Feb. 23, 2009.

(56) References Cited

OTHER PUBLICATIONS

PCT/EP2007/058912 filed on Aug. 28, 2007 International Preliminary Report on Patentability dated Nov. 5, 2008.
PCT/EP2007/058912 filed on Aug. 28, 2007 Search Report dated Nov. 12, 2007.
PCT/EP2007/058912 filed on Aug. 28, 2007 Written Opinion dated Nov. 12, 2007.
PCT/EP2007/059407 filed Sep. 7, 2007 International Preliminary Report on Patentability and Written Opinion dated Mar. 10, 2009.
PCT/EP2007/059407 filed Sep. 7, 2007 International Search Report dated Jul. 3, 2008.
PCT/EP2007/059407 filed Sep. 7, 2007 Written Opinion dated Mar. 10, 2009.
PCT/EP2007/062155 filed on Nov. 9, 2007 Search Report dated Mar. 12, 2008.
PCT/EP2007/062155 filed on Nov. 9, 2007 Written Opinion dated Mar. 12, 2009.
PCT/EP2007/062155 filed on Nov. 9, 2007 International Preliminary Report on Patentability dated Oct. 15, 2008.
PCT/EP2007/063347 filed Dec. 5, 2007 Search Report dated Jun. 10, 2009.
PCT/EP2007/063347 filed Dec. 5, 2007 Written Opinion mailed Jun. 10, 2009.
PCT/EP2007/063347 filed on Dec. 5, 2007 Search Report mailed Feb. 4, 2008.
PCT/EP2008/052121 filed Feb. 21, 2008 International Preliminary Report on Patentability dated Aug. 26, 2009.
PCT/EP2008/052121 filed Feb. 21, 2008 International Search Report dated May 19, 2008.
PCT/EP2008/052121 filed Feb. 21, 2008 Written Opinion dated May 9, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 10/362,040, filed Jun. 27, 2003 Advisory Action dated Dec. 16, 2010.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 10/362,040, filed Jun. 27, 2003 Office Action dated Aug. 18, 2008.
U.S. Appl. No. 10/362,040, filed Jun. 27, 2003 Office Action dated Aug. 2, 2006.
U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/300,985, filed Aug. 6, 2010 Final Office Action dated Aug. 15, 2012.
U.S. Appl. No. 12/300,985, filed Aug. 6, 2010 Non-Final Office Action dated Mar. 15, 2012.
U.S. Appl. No. 12/300,985, filed Aug. 6, 2010 Notice of Allowance dated Nov. 16, 2012.
U.S. Appl. No. 12/301,019, filed Feb. 2, 2009 Advisory Action dated Apr. 27, 2011.
U.S. Appl. No. 12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/373,116, filed Jul. 14, 2009 Advisory Action dated Jul. 26, 2011.
U.S. Appl. No. 12/373,116, filed Jul. 14, 2009 Examiners Answer dated Jan. 3, 2013.
U.S. Appl. No. 12/373,116, filed Jul. 14, 2009 Final Office Action dated Apr. 27, 2011.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 10, 2010.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,102, filed Feb. 19, 2009 Non-Final Office Action dated Nov. 15, 2010.
U.S. Appl. No. 12/438,330, filed Feb. 20, 2009 Advisory Action dated Oct. 14, 2010.
U.S. Appl. No. 12/438,330, filed Feb. 20, 2009 Advisory Action dated Oct. 20, 2011.
U.S. Appl. No. 12/438,330, filed Feb. 20, 2009 Final Office Action dated Aug. 11, 2011.
U.S. Appl. No. 12/438,330, filed Feb. 20, 2009 Non-Final Office Action dated Jun. 7, 2012.
U.S. Appl. No. 12/438,330, filed Feb. 20, 2009 Notice of Allowance dated Sep. 25, 2012.
U.S. Appl. No. 12/438,330, filed Feb. 20, 2009 Office Action dated Aug. 5, 2010.
U.S. Appl. No. 12/438,330, filed Feb. 20, 2009 Office Action dated Mar. 16, 2010.
U.S. Appl. No. 12/438,330, filed Feb. 20, 2009 Office Action dated Mar. 4, 2011.
U.S. Appl. No. 12/438,527, filed Feb. 23, 2009 Advisory Action dated May 24, 2012.
U.S. Appl. No. 12/438,527, filed Feb. 23, 2009 Final Office Action dated Mar. 7, 2012.
U.S. Appl. No. 12/438,527, filed Feb. 23, 2009 Non-Final Office Action dated Jul. 11, 2011.
U.S. Appl. No. 12/440,415, filed Mar. 6, 2009 Final Office Action dated Jan. 10, 2013.
U.S. Appl. No. 12/440,415, filed Mar. 6, 2009 Non-Final Office Action dated Jul. 2, 2012.
U.S. Appl. No. 12/440,415, filed Mar. 6, 2009 Notice of Allowance dated Apr. 3, 2013.
U.S. Appl. No. 12/514,177, filed May 8, 2009 Advisory Action dated Sep. 10, 2012.
U.S. Appl. No. 12/514,177, filed May 8, 2009 Final Office Action dated Apr. 27, 2011.
U.S. Appl. No. 12/514,177, filed May 8, 2009 Final Office Action dated Jul. 11, 2012.
U.S. Appl. No. 12/514,177, filed May 8, 2009 Non-Final Office Action dated Jan. 5, 2011.
U.S. Appl. No. 12/514,177, filed May 8, 2009 Non-Final Office Action dated Mar. 13, 2012.
U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.
U.S. Appl. No. 12/517,096, filed Jun. 1, 2009 Non-Final Office Action dated May 6, 2011.

(56) References Cited

OTHER PUBLICATIONS

U.S. Appl. No. 12/517,096, filed Jun. 1, 2009 Non-Final Office Action dated Nov. 28, 2012.
U.S. Appl. No. 12/517,096, filed Jun. 1, 2009 Notice of Panel Decision dated Mar. 23, 2012.
U.S. Appl. No. 12/528,289, filed Aug. 26, 2009 Non-Final Office Action dated Jan. 27, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated Dec. 17, 2010.
U.S. Appl. No. 12/594,531, filed Oct. 2, 2009 Non-Final Office Action dated May 12, 2011.

* cited by examiner

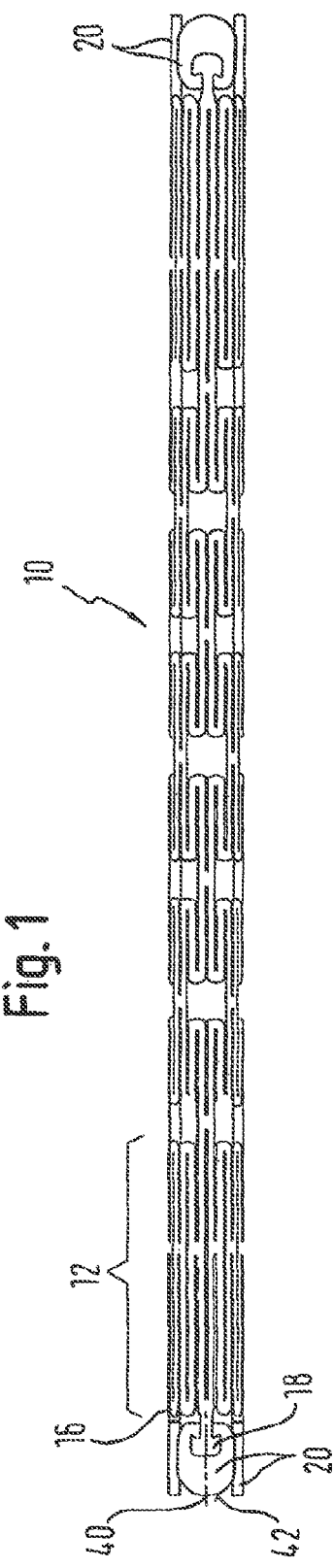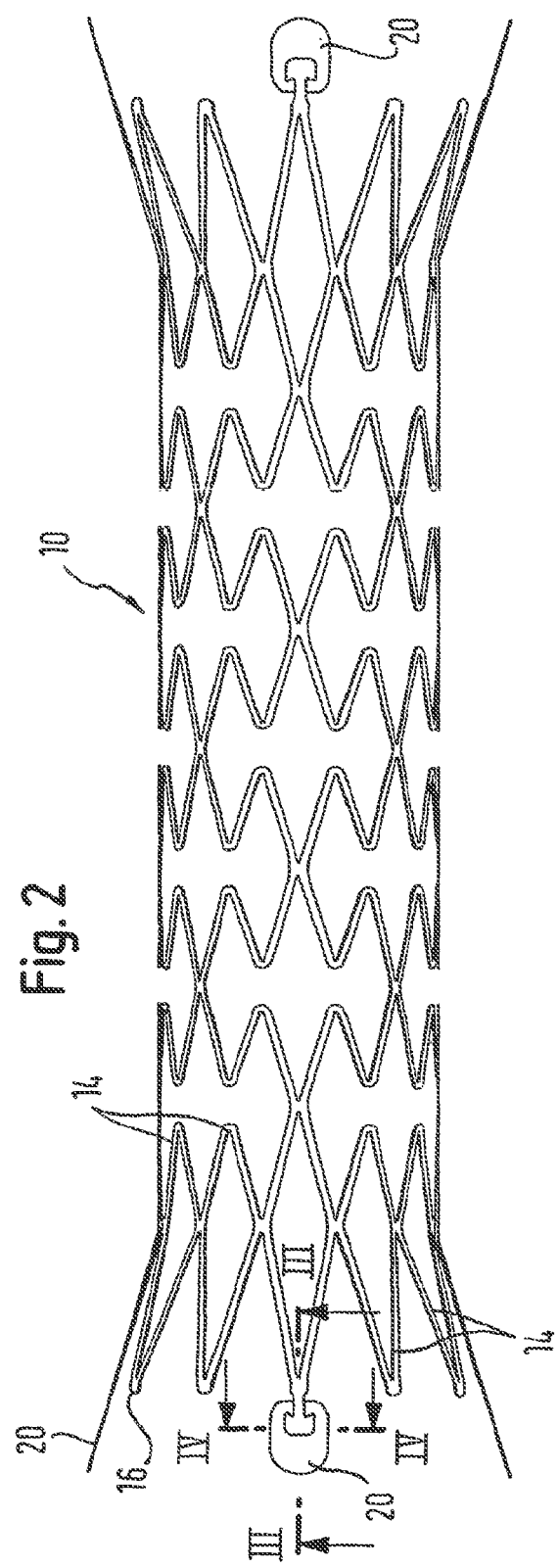

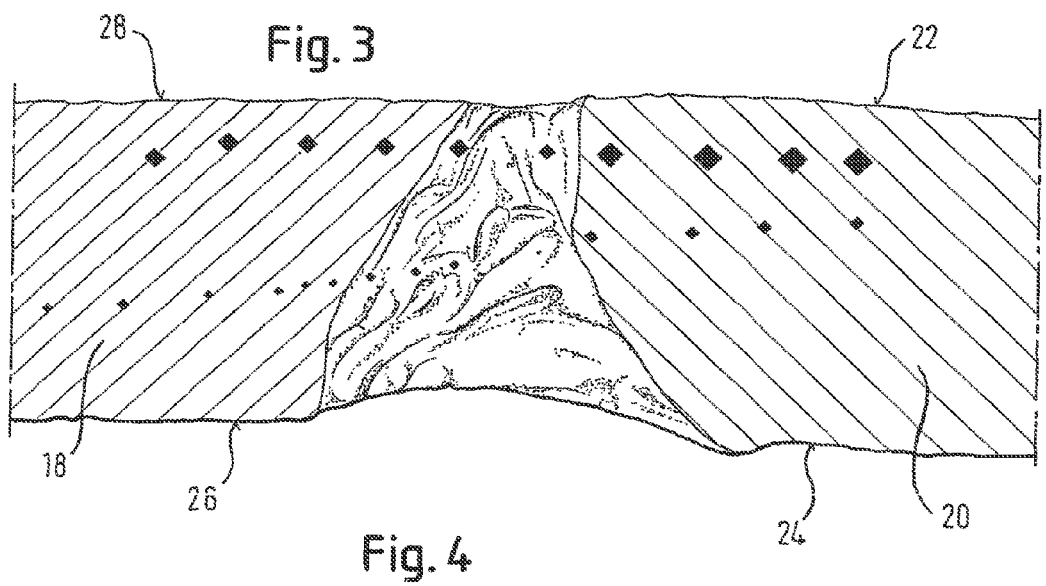
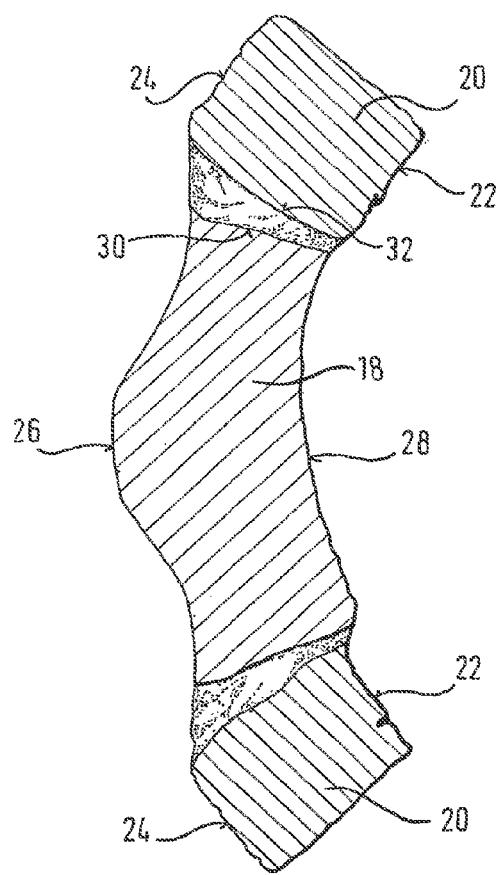

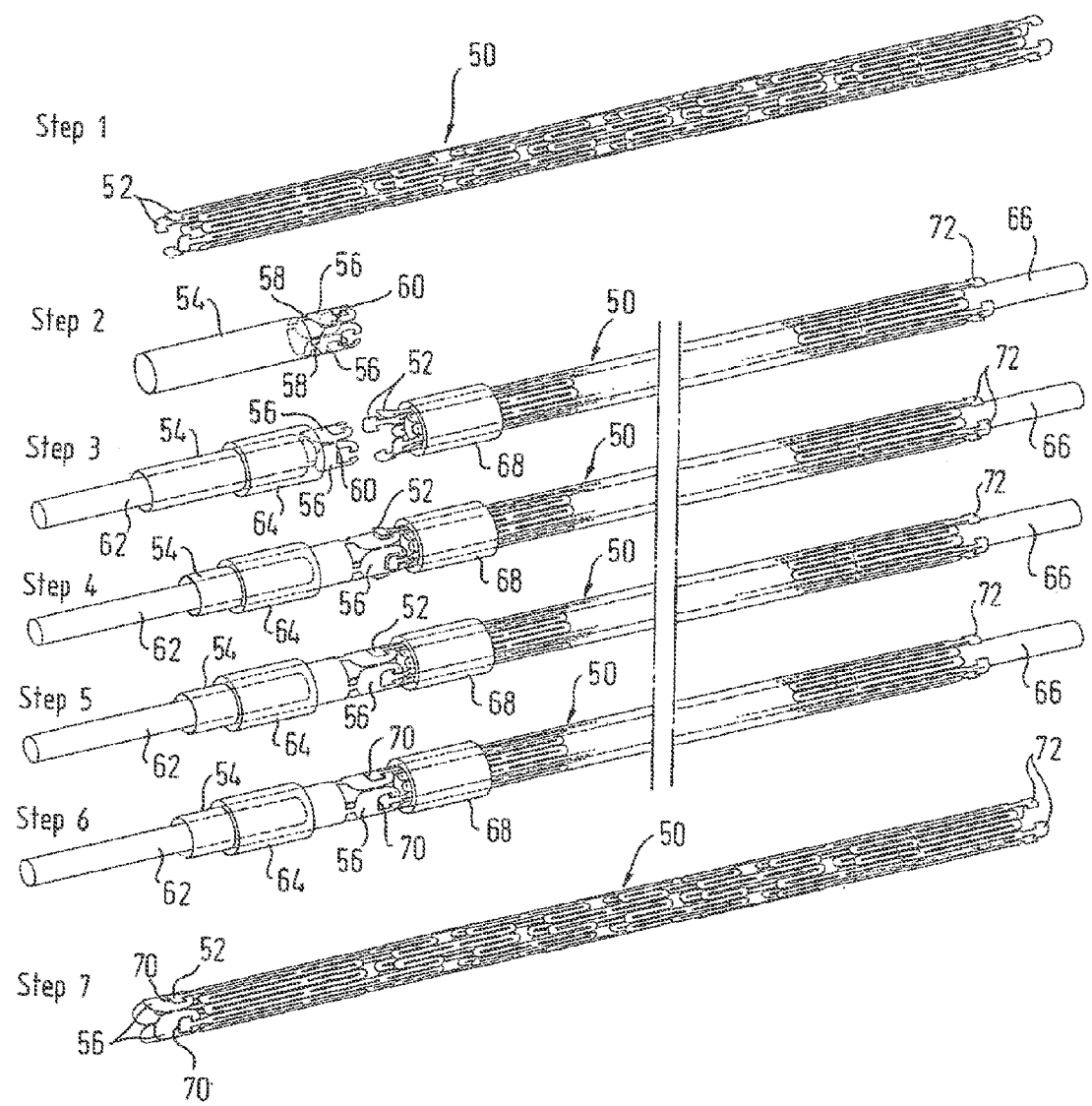

IMPLANT WITH ATTACHED ELEMENT AND METHOD OF MAKING SUCH AN IMPLANT

PRIORITY

This application is a continuation of U.S. patent application Ser. No. 13/279,189, now U.S. Pat. No. 8,900,290, filed Oct. 21, 2011, which is a continuation of U.S. patent application Ser. No. 10/362,040, now U.S. Pat. No. 8,043,364, filed Feb. 18, 2003, which is a U.S. national stage application under 35 U.S.C. §371 of International Application No. PCT/EP01/09467, filed Aug. 16, 2001, claiming priority to United Kingdom Patent Application No. 0020491.7, filed Aug. 17, 2000, each of which is incorporated by reference in its entirety into this application.

FIELD OF THE INVENTION

This invention relates to an implant, such as a stent formed from a stent material, to which is attached at least one element, such as a marker, made from a different material, such as a material having a radiopacity greater than that of the implant material. The invention also relates to a method of making such an implant.

Although the present invention has particular usefulness for attaching radiopaque markers to stents, it also has application to implants (filters, for example) other than stents, and to elements other than markers. Such elements could function as, for example, drug delivery vehicles, trauma inhibitors, or connectors to link the implant to another implant or to an implant extraction tool.

BACKGROUND ART

WO-A-95/03010 discloses a stent in the form of a metal tube having a long axis, a luminal surface and an abluminal surface, and a tube wall thickness, the tube carrying within the wall thickness a radiopaque marker made of a metal more radiopaque than the metal which forms the tube.

The stent of WO 95/03010 is created from a flat sheet of stainless steel material, by photochemical etching away of selected areas of the metal sheet, to leave behind an open lattice-work pattern, which is then rolled up into a tubular shape. A small round opening is provided at each end of the lattice area. Into each of these openings (called "eyelets") can be pressed a radiopaque marker of material such as gold, platinum, tungsten or iridium. The markers are positioned in the eyelets by crimping.

EP-A-800 800 also addresses the problem of poor radiopacity of stents, but advocates a different solution. In a nickel titanium shape memory alloy stent, it is proposed to provide, at one end at least of the cylinder which defines the stent, at least one detection element which has the shape of a tongue extending substantially in the longitudinal direction of the stent, this detection element having a width, in the circumferential direction of the stent cylinder, which is greater than the characteristic width, in the circumferential direction of the stent, of each of the struts which make up the lattice work pattern of the stent. It is the greater circumferential width of the tongue which renders it more radiopaque than the thinner struts of the lattice of the stent.

EP-A-847733 Biotronik discloses a stent which is an apertured cylinder of titanium, to each end of which is welded a meander-form ring of tantalum. The radiopacity of tantalum being much greater than that of titanium, this construction allows the locations of the ends of the stent cylinder to be determined radioscopically.

WO-A-00/64375 ACS was published Nov. 2, 2000, that is, after the present priority date. It discloses a stent made from wire or tube but with end rings of a material more radiopaque that its lengthwise centre section. Materials suggested for the centre section comprise Ni—Ti shape memory alloy (Nitinol) and stainless steel. Materials suggested for the end rings comprise tantalum, platinum, gold and platinum-iridium. To attach the end rings to the centre section, it is suggested to use, inter alia, laser welding.

EP-A-709 068 Medinol discloses providing stent ends with "protrusions having enough metal therein to make them X-ray visible". Gold and tantalum are mentioned as materials which are more visible under X-ray illumination than the stainless steel metal of the stent.

The disclosure of U.S. Pat. No. 6,022,374 is similar to that of WO-A-95/03010 mentioned above, in that it discloses an insert of radiopaque material within an eyelet formed in the stent. Mentioned as radiopaque materials are gold, platinum and alloys thereof.

DE-U-29904817 discloses a stent with axially extending projections at one end, at least. These projections can exhibit a thickening at their outer cantilevered ends. This concept can be compared with the disclosure of EP-A-800800, mentioned above.

U.S. Pat. No. 5,741,327 Frantzen discloses a stent with radiopaque markers attached to the ends of the body of the stent. In one embodiment, a circumferentially continuous serpentine marker element is attached to each end of the stent. This marker element can be of gold, silver, platinum or an alloy thereof. It is disclosed that the body of the stent can be from a nickel-titanium alloy. The circumferential marker is radially expansible along with the body of the stent. A circumferential marker is attached to an end of the stent body using one of a number of techniques including brazing, mechanical fastening, weaving or epoxy adhesive. One specific system of attachment disclosed involves the use of "receivers" that extend from the ends of the stent body. These receivers are configured to receive "tabs" provided on the marker ring. Each tab has a neck and a knob at the end of the neck and the knob is received into a co-operating rounded space of the receiver of the stent body. A laser is used to achieve local melting so that the receiver and tab are fused together.

The disclosures of WO 97/33534 is similar to that of WO 95/03010, in that it includes radiopaque rivets set in a stent of less radiopaque material.

SUMMARY

It is one object of the present invention to provide an implant, such as a stent, with an element of different material, securely fixed to the implant as such.

It is a more particular object of the present invention to provide a nickel-titanium shape memory alloy stent with a radiopaque marker which is compatible with the alloy of the stent; and biologically acceptable, and which is more effective and reliable than previous proposals.

According to one aspect of the present invention there is provided a stent recited in claim 1 below. In a second aspect, there is provided an implant and, in a third aspect, a method of attaching elements to an implant is provided.

With a ring of elements in the form of spoons, attached at one end of a tubular implant such as a stent, a more or less complete ring of attached material is presented in the radially compact delivery disposition of the stent, yielding potentially enhanced radiopacity. Even in the expanded disposition of the stent, a relatively small number of wide area spoons, say four, delivers relatively good radiopacity. However, the radiopacity in the compact disposition is particularly high, so that the present invention opens up the possibility to eliminate the previously indispensable radiopaque marker ring on the stent delivery system which reveals the location of an end of the stent. This in turn opens up the way to make delivery systems which are simpler in construction than the systems used up to now.

If interfitting shapes of the stent ends and attached elements are cut by a laser with its line of action always radial to the stent cylinder, then a tapered or beveled form fit between the stent and each attached element is achieved, enhancing the security of attachment and the precision of placement of each element attached to the stent.

This tapered form fit is particularly helpful when it is such that disengagement of the form-fit occurs by a radially-outward movement of the element relative to the stent cylinder. This is because, when the stent expands into its installed configuration, there is radially-inward pressure on the attached element from the surrounding bodily tissue, which resists its disengagement from the stent. This resistance complements and reinforces whatever other system is employed to fix the element to the stent.

Systems to fix an element to an implant can include welding, brazing, soldering, glueing, friction welding or variations of mechanical interlocks and press-fit configurations.

When creating stent lattices from sheet material, tubular sheet starting material is often considered advantageous. However, flat sheet material also is advantageous in some systems, such as those in which the stent element is rolled up like a carpet. When laser-cutting the lattice, the above-mentioned tapered form fit can be readily engineered when cutting the sheet in planar form.

In a particularly advantageous embodiment, a stent is formed from sheet material in the form of a tube, and is provided at each end with a plurality of marker carrier portions, to each of which is mounted a radiopaque marker of radiopaque material, in the form of a spoon. Each of the carriers has a luminal surface, an abluminal surface, and a peripheral surface through the thickness of the stent tube. It is this peripheral surface which provides one of two complementary mating surfaces for making the stent/marker attachment. The complementary marker itself has two major surfaces, one of which is luminal and the other is abluminal, and a peripheral surface around the major surfaces. However, within the area of the major surfaces is a cavity portion. The periphery of this cavity defines a female element for engagement with a male portion of the stent tube marker carrier portion, the male and female peripheral surfaces providing complementary tapering form-fit surfaces.

Preferably each such ring of markers has four marker spoons in it. Increasing beyond four reduces the size of each marker. In the expanded configuration of the stent, visibility of the stent increases with the physical area of each separate marker, so large markers are preferred because they make the expanded stent more visible.

It is preferred that the markers together make a more or less continuous ring around the stent in its small diameter configuration prior to its deployment by expansion.

According to the second aspect of the present invention there is provided a method for making from sheet material a tubular implant, such as a stent, which expands, during its deployment, from a smaller radius delivery disposition to a larger radius deployed disposition, the method comprising the steps of:

1. providing at least one terminal element on one end of a support of sheet material arranged as a cylinder with its radius being that of the said delivery disposition;
2. presenting the tubular implant in its smaller radius, end-to-end with the support, such that the terminal element abuts the implant;
3. fixing the terminal element to the implant; and
4. parting the terminal element from the support.

One of the problems involved in fixing radiopaque markers to stents is the difficulty of aligning the markers with the stent in order to fix the markers to the stent in exactly the right orientation and position relative to the stent as such. This second aspect of the invention ameliorates this problem by presenting markers as terminal elements on one end of a cylindrical support of sheet material which has the same radius as the stent in its unexpanded disposition. This is because it is relatively easy to arrange in co-linear fashion the cylinder of the stent and the cylinder of the support and, with both of these items having the same radius, the cylindrical end surface of the support would be in abutment with the cylindrical end surface of the stent. Now, if the cylindrical end surface of the support exhibits a plurality of terminal elements which are destined to become elements attached to the stent, the process of fixing these markers to the stent can be effected by welding the elements to the end of the stent, while they are in end-to-end abutment with the stent end. Then, when this welding step has been completed, it should be a simple further step to part the marker elements from the support cylinder, for example, by laser-cutting through the thickness of the sheet material which forms the support.

It will be appreciated that the terminal elements will have the curvature of the support cylinder, which curvature will correspond to the curvature of the stent in its delivery disposition. Thus, when the stent expands to its deployed disposition, and the curvature of the terminal elements remains unchanged, these elements will have a radius of curvature somewhat smaller than the radius of the expanded stent cylinder. However, this discrepancy in curvature will not be significant because the terminal elements will be, to a greater or lesser extent, embedded in the bodily tissue forming the wall of the lumen in which the stent is deployed. Indeed, the elements might have no curvature at all. This would be the case if, for example, the main stent manufacturing steps are performed on flat sheet material, while it is planar, with the stent lattice then being rolled up for installation into a delivery system. The rolling up step would impart a curvature to the stent, but not necessarily to the attached elements.

The invention is particularly well adapted to the technical field of shape memory alloy stents, specifically those made of Nitinol, and the attachment to them of terminal marker elements of tantalum.

In order to make Nitinol stents more visible to radiation, by the provision of tantalum markers, one would wish to import a greater mass of tantalum, but without any increase in the wall thickness of the stent at the locations of the markers. The ideal stent has minimal wall thickness, not only for keeping the stented bodily lumen as open to fluid as possible, but also to keep the stent delivery system with as small a cross-sectional profile as possible. The present invention furthers this objective, in the following way.

The cylinder of sheet material which provides the terminal elements and support tube is amenable to laser-cutting of the terminal elements out of the material of the tube. Accordingly, virtually all of the material forming the circumference of the tube is available for contribution to the making of the terminal elements. The terminal elements can take up the entire circumference of the support tube, except for the thickness of the laser cuts between adjacent terminal elements around the circumference. Accordingly, for the stent in its small radius delivery disposition, there could be virtually an entire circumference of radiopaque tantalum marker material provided at each end of the stent, with the only breaks in the continuous ring around the circumference being the laser cuts between adjacent marker elements.

In one specific embodiment, there is laser-cut from the support tube a pattern of four terminal marker elements, each extending around one quarter of the circumference of the support tube. Each of these marker elements takes up virtually ninety degrees of the circumference of the stent in its delivery disposition.

The exact shape of the outline of each terminal element, and the exact shape of the abutment surface on it which contacts the corresponding abutment surface of the end of the implant, is a matter of design freedom and choice. At the moment, for implants which are stents, and attached elements which are radiopaque markers, it is contemplated to provide each element with more or less straight sides to face the adjacent marker elements around the circumference of the stent, but with an arcuate end surface and a female rebated internal abutment surface to receive a corresponding arrowhead shape male marker carrier portion on the end ring of the stent. Such a pattern of shape features is described in more detail below by reference to the accompanying drawings.

With a male/female interfit of the marker element and stent end ring carrier portions, with rebated surfaces, and with the respective peripheral mating surfaces extending along radial lines to the stent cylinder, a snap fit interengagement of the stent cylinder and support cylinder can be arranged, further helping to accomplish the objective of precise position and orientation of the marker elements relative to the stent cylinder.

In any event, a convenient way to fix permanently and reliably the tantalum marker elements to a Nitinol stent cylinder is by laser-welding. When laser-cutting the lattice of a stent from a cylinder of sheet material, the line of action of the laser is invariably on a radius of the tubular workpiece. If the co-operating surfaces of the stent, and of its spoons, end elements or markers, are both cut with a laser on a radial line of action, then there will tend to be a self-centering and self-aligning effect when the support tube is offered up, end-to-end to the stent in its small radius of compressed configuration. This effect enhances the value of the method of the present invention in building stent assemblies to precise tolerances and with its end elements securely attached.

For a better understanding of the present invention, and to show more clearly how the same may be carried into effect, reference will now be made, by way of example, to the accompanying drawings.

BRIEF DESCRIPTION OF THE DRAWINGS

FIG. 1 is a view from the side of a stent tube, looking along a line which intersects the long axis of the tube and is perpendicular to it the stent being in its smaller radius delivery configuration; and FIG. 2 is the view of FIG. 1, but with the stent in its deployed, relatively large radius disposition;

FIG. 3 is a micrograph taken on a section through the line III-III shown in FIG. 2;

FIG. 4 is a micrograph taken on a section through the line IV-IV shown in FIG. 2; and FIG. 5 shows schematically a stepwise manufacturing process.

DETAILED DESCRIPTION

Skilled readers will appreciate that the material of the stent tube and its markers lies all in a circular cross-section with a wall thickness as small as possible, so as to be consistent with the objective of maintaining a bodily lumen as open as possible. The stent cylinder can be formed from seamless tubular starting material, or from flat material rolled into a tube (which thus exhibits some sort of seam).

Skilled readers will also be well aware that there have been a very large number of proposals for strut patterns in the tubular configurations of stents. Whereas FIG. 1 shows an expandable strut pattern in a form which is particularly preferred for the present Applicant, nevertheless any other strut pattern will have points in it which define an end to the cylinder of the stent, and therefore will have points at the ends of the stent cylinder where markers can be attached.

Readers will also appreciate that self-expanding stents are delivered to stenting locations in a radially compressed form, so that the aggregate length, in the circumferential direction, of all of the markers in any particular ring around the axis of the stent tube cannot exceed the circumference of the stent tube in its compressed delivery configuration. In the embodiment shown in FIG. 1, each of the four markers has a circumferential length just less than the circumferential length of three cycles of the zigzag pattern which defines the end ring of the stent cylinder so that, when the stent cylinder is compressed, with all the struts of the zigzag ring laying close to each other, the adjacent radiopaque markers will also lie closely adjacent each other in the circumferential direction.

As can be seen in FIG. 1, the end ring 12 of the stent cylinder 10 is constituted by a succession of struts 14 which zigzag their way around the full circumference of the ring 12. There is a vertex 16 where each two successive struts intersect, with the end of the stent cylinder being defined by the succession of vertices 16. A marker carrier portion 18 is located at every third end vertex 16, and fitted to each carrier portion 18 is a marker element 20. In the illustrated embodiment, the stent is made from Nitinol, nickel-titanium shape memory alloy, and each marker element is of tantalum. In other embodiments, the stent could be of stainless steel. The attached elements could be of tantalum, platinum, gold or iridium, for example.

Referring now to FIGS. 3 and 4 together, the tantalum marker 20 has a luminal surface 22 and an abluminal surface 24, with the abluminal surface 24 being in line with the abluminal surface 26 of the stent cylinder and the luminal surface 22 of the marker being in line with the luminal surface 28 of the stent cylinder. FIG. 4 shows that the peripheral surface 30 of the carrier portion 18 is tapered inwardly from the abluminal surface 26 to the luminal surface 28 of the stent cylinder. The marker 20 has a co-operating complementary tapered mating surface 32, therefore also defining part of a cone with its vertex lying radially inside the stent cylinder. It will be appreciated that achievement of the form fit-shown in FIG. 4 is by advancing the carrier portion 18 radially inwardly into the cavity defined by surface 32 of the marker 20 until there is a tight fit between the two complementary tapered surfaces 30 and 32, corresponding with a lining up of the luminal and abluminal surfaces of the stent cylinder and marker.

In FIG. 4 surfaces 24 and 26 face a bodily lumen wall. The stent cylinder 10 with its end ring 12 and its carrier portions 18 are serving to hold back the bodily lumen wall tissue from radially inward encroachment (rightwards in FIG. 4). The tissue presses radially inward also on the marker 20, tending to dislodge the form-fit. However, in laser-welding the tantalum spoon 20 to the Nitinol carrier portion 18, melting and flow of Nitinol around the tantalum spoon achieves re-entrant locking surfaces, as can be seen on the photomicrograph, which effectively resist such dislodging.

The present invention aims to assist the attachment of tantalum markers to Nitinol stents, for example by laser-welding, and make it even more reliable and secure. The melting point of tantalum is around 3000° C., and that of Nitinol around 1200° C., rendering it difficult to achieve a good bond purely by welding. However, the tapered close fit between the two metals, and the flow of Nitinol around the tantalum during welding, achieves a secure mechanical interlock between the stent and the marker 20.

It is conventional to form the lattice patterns of Nitinol stents by laser-cutting. The line of action of a laser for cutting the tapered mating surfaces 30 of the carrier portion 18 in the stent are achieved by aligning the laser in the normal radial direction of intersecting the long axis of the stent tube As to the number of markers in one circumference of the stent, optimum radiopacity is accomplished when the markers at each end of the stent make up a virtually unbroken solid ring of marker material around the full circumference. In the case shown there is a marker on every third end vertex of the stent, with 4 markers at each end of the stent, and 12 zigzag vertices around the circumference of the stent. This, however, is not to exclude the possibility of fewer markers at each end of the stent, including the extreme case, seen in wo 95/03010, mentioned at the beginning of this specification, that there is only one marker at each end of the stent cylinder.

Turning now to the second aspect of the invention, and to the assembly of the markers 20 onto the stent 10, one can see from FIG. 1 how the four markers 20 at each end of the stent cylinder form a virtually unbroken ring of material having a diameter exactly the same as that of the stent cylinder 10 in the delivery disposition of FIG. 1.

FIG. 5 shows the four adjacent markers 56 are all cut from a single tube of tantalum material having the same radius as the stent cylinder 10, a laser having been used to cut around the periphery of each marker, including the rebated portion in the centre of the marker which receives the marker portion 18 of the stent. The only place where the thus cut marker element 56 remains attached to the carrier tube is at the central tip 40 (FIG. 1) of the arcuate surface 42 which defines the peripheral end surface of the marker 20 remote from the stent cylinder 10.

A support cylinder 54 which includes the four markers 20, 56 attached at their tips 40 is offered up to the stent cylinder 10, the two cylinders being co-linear and coaxial. There is then a snap fit of the marker portions 18 of the stent 10 into the receiving recess of each marker 20. Once the marker portions 18 are secure within the recesses of the respective markers 20, a laser can be deployed to produce a laser weld between the marker portion 18 and the marker 20. During welding; the Nitinol adjacent the tantalum marker melts locally and to a limited extent flows around the tantalum, thereby effectively form-locking the marker to the stent. With this laser welding accomplished, a laser can then be brought into play, to part at marker tip 40 each individual marker 20 from the carrier tube 54 which has supported it up to that point. With this parting away of the markers 20 from their carrier tube, the stent can then be separated from the carrier tube, with the markers 20 securely welded to the stent 10.

Readers will immediately appreciate from the above description, taken in conjunction with the drawings, that the markers 20 have the general form of a spoon. That is to say, the markers have two major dimensions and one minor dimension, namely, the thickness in the radial direction of the stent. The two major surfaces have a length direction in the length direction of the stent and are more or less flat in that direction. However, in the transverse direction, circumferential with respect to the stent cylinder, the markers are curved so that they exhibit a luminal surface which is concave and an abluminal surface which is convex. This curvature is also exhibited in the transverse direction of a cutlery spoon.

Further, each marker 20 has a near end surface in which is something akin to the shaft of a cutlery spoon, namely, the marker portion 18 of the stent. Opposite this end surface is another end surface, relatively remote from the stent, which is not attached to the stent and is arcuate on its periphery. This is reminiscent of the arcuate (in the sense of presenting an outwardly convex shape) peripheral end surface of a cutlery spoon, remote from the shaft of the spoon.

In FIG. 5 are shown seven steps, in FIGS. 5(1) to 5(7), of a process for manufacturing an implant in accordance with the invention, which is a stent of Nitinol having at each of its ends a ring of tantalum spoons.

Step 1 is to cut with a laser a tube of Nitinol material in order to produce a stent precursor 50 having at each ends a ring of four marker carrier portions 52 each having a shape which has some slight resemblance to an arrowhead shape. In the example shown here, the Nitinol tube has a wall thickness of 0.24 mm and a nominal diameter of 1.6 mm.

FIG. 5(2), showing step 2, shows a tube of tantalum 54 which has the same 1.6 mm nominal diameter and 0.24 mm wall thickness but a shorter length than the stent precursor 50. At one end of the tantalum tube 54 has been laser-cut a ring of four spoons 56. A narrow bridge of material 58 at the tip 40 on the arcuate end surface of each spoon connects each spoon 56 to the tube 54, and a similar narrow bridge 60 links each spoon 56 at its widest point to the corresponding point on the next adjacent spoon 56 on each side. In this way, the spoons are all linked up in a ring and each individually still part of the tantalum tube 54.

In FIG. 5(3), step 3 of the manufacturing process includes placing a core 62 inside the tantalum tube 54, and a surrounding sleeve 64 radially outside the tube 54. The core 62 and sleeve 64 do not extend as far as the ring of spoons 56 but terminate just short of that ring. Likewise, Nitinol tube 50 receives a core 66 and a surrounding sleeve 68 which again stop just short of the ring of carrier portions 52. In a jig, the two spaced cores 62 and 66 are linked through their outer ends so as to be maintained co-axial and co-linear, which therefore assures that the ring of carrier portions 52 and ring of spoons 56 are themselves co-axial and co-linear. FIG. 5(3) shows each of the carrier portions 52 tilted slightly radially outwardly, to indicate that this is feasible, for offering up the carrier portions 52 into the corresponding recesses of the corresponding spoons 56, as explained above, and as shown in FIG. 5(4).

In FIG. 5(4), it is shown how manual manipulation of the carrier portions 52 can be used to get them into the corresponding recesses of the spoons 56, when the cores 62 and 66 are brought closer to each other in the above-mentioned jig. This manual manipulation, of each individual carrier portion 52 in turn, is carried out manually, under a microscope.

FIG. 5(5) shows the carrier portions 52 duly fitted within the corresponding recesses of the spoons 56.

FIG. 5(6) differs from the preceding method step of FIG. 5(5) by the presence of a welding bead 70 which connects each one of the spoons 56 with its corresponding carrier portion 52, around the periphery of the arrowhead of the carrier portion 52. This welding bead is a result of a laser-welding step which occurs between illustrated steps 5 and 6 but is not shown as such in FIG. 5. In itself, it will be familiar to readers skilled in Nitinol stent manufacture.

FIG. 5(7) differs from FIG. 5(6) in that the cores 62 and 66 and the rings 64 and 68 have been removed, to leave a ring of spoons 56 duly welded to one end of the Nitinol tube stent precursor 50. With a laser, the bridges 58 and 60 are cut through, so as to release each spoon from the tantalum tube 54 and the spoons adjacent to it.

Clearly, if it desired to place a ring of spoons at the other end of the stent tube 50 then the process can be repeated at this other end. Indeed, in FIG. 5, a ring of carrier portions 72 is shown at the other end of the stent tube 50.

Once the spoons have been placed as desired on the precursor tube 50 of the stent, then this precursor tube can be subjected to the normal successor manufacturing steps, including the step of expanding the stent precursor to a desired larger diameter and then annealing it at that diameter in order to "set" a stent shape in the austenitic phase of the Nitinol material, which is the shape that it is desired the stent should revert to, in the body, upon deployment from a stent delivery system. Such a set shape might include a central cylindrical portion of the stent, and flared portions at each end, with the ring of carrier portions 52 and spoons 56 themselves forming part of the flared portion of the end of the stent. As tantalum has a melting point so much higher than that of Nitinol, there is no likelihood that the Nitinol annealing step will in any way adversely affect the spoons and welding beads at each end of the stent cylinder.

The scope of protection of the claims which follow is not to be limited to the embodiments described in detail above. Readers will appreciate that the detailed description is to assist in realising embodiments within the scope of the claim rather than to set a limit on the scope of protection.

What is claimed is:

1. A stent, having:
    an axial end; and
    a ring of spoons connected to the axial end through a plurality of complementary male-female form-fitting portions, the ring of spoons comprising:
        parallel straight side edges; and
        a material different from a material composing the stent, wherein:
            the stent expands from a delivery configuration to a deployed configuration and the diameter of the deployed configuration is greater than the diameter of the delivery configuration; and
            each of the side edges lies within a first distance from a facing side edge of an adjacent spoon in the delivery configuration, and each of the side edges lies within a second distance, greater than the first distance, from the facing side edge of an adjacent spoon in the deployed configuration.

2. The stent according to claim 1, wherein the material of the ring of spoons is tantalum.

3. The stent according to claim 2, wherein the material composing the stent is either stainless steel or a nickel-titanium shape memory alloy.

4. The stent according to claim 1, wherein the ring of spoons is attached to the stent via laser-welding.

5. The stent according to claim 1, wherein each spoon of the ring of spoons has an axial length between a first end and a second end, the first end having the form-fitting portion and the second end having a convex shape.

6. The stent according to claim 1, wherein each spoon of the ring of spoons has a luminal major surface and an abluminal major surface, each of the major surfaces being arcuate and within a cylindrical envelope which corresponds to the delivery configuration.

7. The stent according to claim 6, wherein each spoon of the ring of spoons extends around about one quarter of a circumference of the stent.

8. The stent according to claim 1, wherein the ring of spoons are radiopaque markers.

9. The stent according to claim 1, wherein the complementary male-female formfitting portions have complementary tapered mating surfaces lying in a plane that intersects a longitudinal axis of the stent.

10. The stent according to claim 9, wherein the tapered mating surfaces constitute the female portion of the male-female form-fitting portions.

11. The stent according to claim 10, wherein each of the tapered mating surfaces has a barbed, arrowhead shape.

12. The stent according to claim 11, wherein the ring of spoons is attached to the stent via laser-welding.

* * * * *